(12) United States Patent
Bloemer et al.

(10) Patent No.: US 6,352,631 B1
(45) Date of Patent: Mar. 5, 2002

(54) GAS SENSOR

(75) Inventors: Bernhard Bloemer; Rainer Strohmaier; Carsten Springhorn, all of Stuttgart; Detlef Heimann, Gerlingen; Margret Schuele, Weil Der Stadt; Bernd Schumann, Rutesheim, all of (DE)

(73) Assignee: Robert Bosch, GmbH, Stuttgart (DE)

( * ) Notice: Subject to any disclaimer, the term of this patent is extended or adjusted under 35 U.S.C. 154(b) by 0 days.

(21) Appl. No.: 09/476,842

(22) Filed: Jan. 3, 2000

(30) Foreign Application Priority Data

Jan. 2, 1999 (DE) .......................................... 199 00 017

(51) Int. Cl.$^7$ ............................................. G01N 27/407
(52) U.S. Cl. ...................... 204/424; 204/408; 204/421
(58) Field of Search ................................ 204/421–429, 204/408

(56) References Cited

U.S. PATENT DOCUMENTS

| 3,400,054 | A | * | 9/1968 | Ruka et al. |
| 3,451,859 | A | * | 6/1969 | Zysk et al. |
| 3,468,780 | A | * | 9/1969 | Fischer |
| 3,767,469 | A | * | 10/1973 | Flais et al. |
| 4,902,400 | A | * | 2/1990 | Usami et al. |
| 5,897,759 | A | * | 4/1999 | Kurosawa et al. .......... 204/424 |

FOREIGN PATENT DOCUMENTS

JP          53-45480          * 10/1979

OTHER PUBLICATIONS

Fitzgerald et al, "Basic Electrical Engineering", 2d Ed., (1957), Month Unavailable pp. 466, 467, 474–477.*

* cited by examiner

Primary Examiner—T. Tung
(74) Attorney, Agent, or Firm—Kenyon & Kenyon

(57) ABSTRACT

A gas sensor in the form of a mixed-potential sensor in which the influence of temperature-dependent interference is reduced. An improved temperature control is provided with the help of a temperature sensor mounted on the surface of the electrolytic substrate.

9 Claims, 1 Drawing Sheet

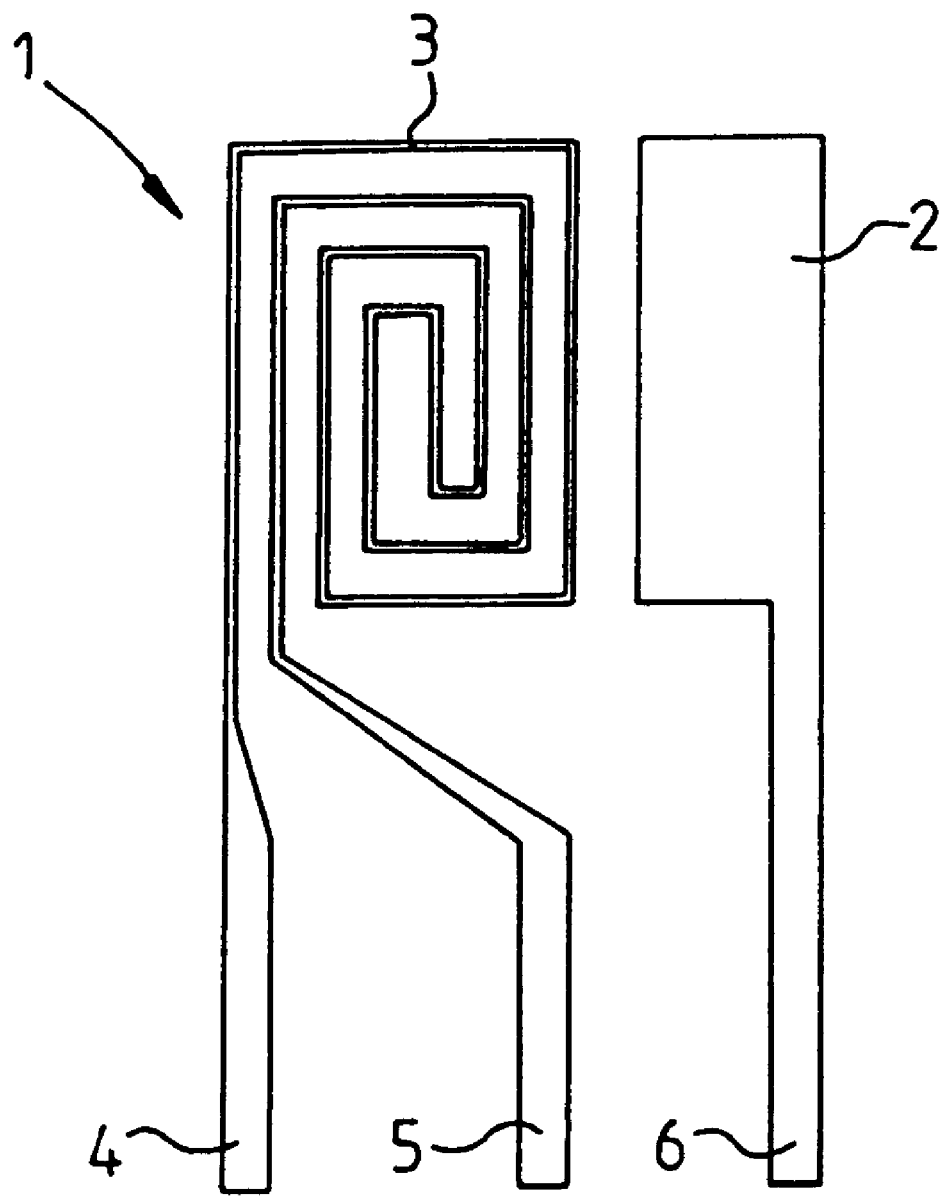
Fig.

GAS SENSOR

BACKGROUND INFORMATION

Known gas sensors, used for example to test automobile exhaust gases, have two electrodes that are mounted on an electrolytic substrate. A zirconium dioxide substrate, on which a metal-oxide electrode and a platinum reference electrode are mounted, is normally used for this purpose. Upon contact with the gas to be analyzed, surface reactions occur on the metal-oxide electrode, after which ions are formed, with these ions migrating through the electrolyte. In an arrangement like the one described above, $O_2^-$ ions are formed and migrate through the zirconium dioxide used as the electrolyte. The flow direction of this ion migration is determined by the respective potentials at the electrodes on both sides of the arrangement when a certain gas composition is present. A difference in potential can therefore be measured between the two electrodes in the form of an electric voltage, and conclusions about the gas composition can be drawn on this basis.

Because different gas components contribute to the formation of signals at the metal-oxide electrode, the latter is referred to as a mixed-potential sensor. The influences of the different gas components on the sensor signal are just as dependent on temperature as the overall intensity of the measurement signal.

To use a sensor of this type for a specific gas, it is therefore important to know the sensor temperature. The ability to set a specific temperature, i.e., using a temperature controller, is especially advantageous.

This has therefore been taken one step further and integrated a heating element and a temperature sensor into the electrolytic substrate.

SUMMARY OF THE INVENTION

An object of the present invention is to provide a gas sensor which reduces interference caused, for example, by different temperatures within the electrolytic substrate, thereby obtaining a more useful sensor signal.

A gas sensor according to the present invention having two electrodes that are provided on the surface of an electrolytic substrate is thus distinguished by the fact that a temperature sensor is also provided on the surface of the electrolytic substrate. This temperature sensor, which is positioned as close as possible to the electrodes, is able to precisely measure the surface temperature of the foil substrate in the direct vicinity of the sensor electrodes, in particular in the direct vicinity of the electrode at which the reactions with the gas to be measured take place, leading to the formation of the measurable difference in potential.

According to one particular embodiment, this electrode is designed as a metal-oxide electrode and mounted on a substrate made of zirconium dioxide. This enables the reaction mechanism to take place, i.e., the formation of reactions in the gases coming into contact with the surface of the metal-oxide electrode and the conduction of these $O_2^-$ ions to a corresponding counter-electrode. This counter-electrode is provided in the form of a reference electrode made of a material that is as chemically inert as possible, for example a noble metal such as platinum.

According to one advantageous embodiment of the present invention, the temperature sensor is provided on the surface of the electrolytic substrate in PTC form, i.e., a temperature-dependent electrical resistor. Among other things, this enables a temperature to be measured when a defined voltage is applied to both sides of this conductor.

According to one particular embodiment of the present invention, the temperature sensor is mounted on the electrolytic substrate in the form of a printed conductor. A printed conductor of this type can be mounted with the usual surface-working techniques.

This printed conductor is advantageously provided with a pattern which lengthens the conductor without greatly increasing the distance between the sensor electrodes. A pattern of this type can be achieved, for example, with a waved shape. In addition to lengthening the printed conductor, a parallel conduction of current in the opposite direction through a wave of this type simultaneously reduces the electromagnetic fields produced by the current flow, thus preventing any further interference from being generated.

According to one particularly advantageous embodiment of the present invention, the temperature sensor is formed by one of the two electrodes. For this purpose, the temperature sensor is used to measure the temperature in the direct vicinity of the electrode, and the number of external contacts needed to operate the sensor is also reduced by designing the temperature sensor to function simultaneously as a gas sensor electrode. By using the temperature sensor as an electrode, only two connections are needed overall instead of two separate connections for the temperature sensor and one connection for the electrode.

In particular, the temperature sensor measures the temperature at the electrode's exact location, thus making it possible to measure the average electrode temperature with particular accuracy.

The temperature sensor according to the present invention can also conceivably be designed as a catalytic detector that can detect the reaction heat.

A potential-free power supply is preferably provided, so that the voltage applied to the temperature sensor does not interfere with the sensor signal.

BRIEF DESCRIPTION OF THE DRAWING

The FIGURE shows a schematic representation of a gas sensor according to the present invention.

DETAILED DESCRIPTION

As shown in the FIGURE, gas sensor 1 includes a metal-oxide electrode 2, which is mounted opposite a wave-shaped reference electrode 3, preferably made of platinum. Reference electrode 3 is thus provided with two contacts 4, 5. The potential of the metal-oxide electrode can be tapped via a further contact 6.

Both electrodes 2, 3 are mounted, for example, on a zirconium dioxide substrate.

During sensor operation, the gases to be measured come into contact with both electrodes 2, 3 in the form of a mixture. Chemical reactions then take place on metal-oxide electrode 2. Depending on the gas type, an $O_2^-$ ion is formed from oxygen molecules $O_2$ or neutral oxygen molecules are released on the basis of $O_2^-$ ions. The $O_2^-$ ions migrate through the electrolytic substrate, with the flux direction of this ion migration being derived from the difference in potential between electrodes 2, 3. As in the case of galvanic cells, a series of voltages, from which the different potentials and thus the sign and magnitude of the voltage forming between electrodes 2, 3 are derived, therefore exists for the gases to be measured in connection with the gas sensor.

This voltage can be tapped, for example, between contacts 5, 6, while a constant voltage is applied between contacts 4, 5 using a potential-free power supply. The temperature can be measured directly at the electrode location using the current flowing through electrode 3 between contacts 4, 5. The corresponding sensor signal can be tapped via the difference in potential between electrodes 5, 6. The use of a separate heating device, for example inside the substrate, thus makes it possible to measure the temperature independently of the necessary heat output.

In addition, the reference electrode can undergo a selective current activation step without this having a negative impact on metal-oxide electrode 2.

According to the present invention, a mixed-potential sensor of the type described can be provided with a precise temperature control means, thus improving the accuracy of the specific gas measurement.

What is claimed is:

1. A gas sensor comprising:

an electrolytic substrate having a surface;

two electrodes situated on the surface of the electrolytic substrate; and a temperature sensor situated on the surface of the electrolytic substrate to measure a temperature at a location of the electrodes, wherein the temperature sensor includes:

a temperature-dependent electrical resistor; and one of the two electrodes.

2. The gas sensor according to claim 1, wherein the temperature sensor is applied to the electrolytic substrate in the form of a printed conductor.

3. The gas sensor according to claim 2, wherein the printed conductor has a pattern for lengthening the conductor within a defined surface area.

4. The gas sensor according to claim 3, wherein the pattern is wave-shaped.

5. The gas sensor according to claim 1, further comprising a controllable power supply coupled to the temperature sensor.

6. The gas sensor according to claim 5, wherein the power supply is potential-free.

7. The gas sensor according to claim 1, wherein the one of the two electrodes included in the temperature sensor is a reference electrode composed of platinum.

8. The gas sensor according to claim 1, wherein the electrolytic substrate is at least partially composed of zirconium dioxide.

9. The gas sensor according to claim 1, wherein the other of the two electrodes is a metal-oxide electrode.

* * * * *